United States Patent
Jo et al.

(10) Patent No.: US 10,736,929 B2
(45) Date of Patent: Aug. 11, 2020

(54) METHOD FOR PREPARING HERBAL COMPOSITION HAVING INCREASED FAT-SOLUBLEPOLYPHENOL CONTENT, HERBAL COMPOSITION PREPARED THEREBY AND USE THEREOF

(71) Applicant: KOREA ATOMIC ENERGY RESEARCH INSTITUTE, Daejeon (KR)

(72) Inventors: Sung-Kee Jo, Jeollabuk-do (KR); Hae Ran Park, Jeollabuk-do (KR); Uhee Jung, Gyeonggi-do (KR); Ho Yong Lee, Gyeonggi-do (KR); Hyang Hee Cho, Gwangju (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 65 days.

(21) Appl. No.: 15/760,593

(22) PCT Filed: Oct. 10, 2016

(86) PCT No.: PCT/KR2016/011314
§ 371 (c)(1),
(2) Date: Mar. 15, 2018

(87) PCT Pub. No.: WO2017/061840
PCT Pub. Date: Apr. 13, 2017

(65) Prior Publication Data
US 2019/0038690 A1    Feb. 7, 2019

(30) Foreign Application Priority Data

Oct. 8, 2015  (KR) .................. 10-2015-0141824

(51) Int. Cl.
| | | |
|---|---|---|
| *A61K 36/23* | (2006.01) |
| *A61K 36/65* | (2006.01) |
| *A61K 36/00* | (2006.01) |
| *A61K 36/232* | (2006.01) |
| *A61K 31/352* | (2006.01) |
| *A61K 31/7048* | (2006.01) |
| *A61K 36/234* | (2006.01) |
| *A23L 33/105* | (2016.01) |
| *A61P 35/00* | (2006.01) |
| *A61P 37/04* | (2006.01) |
| *A23L 33/10* | (2016.01) |
| *A61K 31/192* | (2006.01) |
| *B01D 11/02* | (2006.01) |

(52) U.S. Cl.
CPC ............ *A61K 36/232* (2013.01); *A23L 33/10* (2016.08); *A23L 33/105* (2016.08); *A61K 31/192* (2013.01); *A61K 31/352* (2013.01); *A61K 31/7048* (2013.01); *A61K 36/234* (2013.01); *A61K 36/65* (2013.01); *A61P 35/00* (2018.01); *A61P 37/04* (2018.01); *B01D 11/0288* (2013.01); *A23V 2002/00* (2013.01); *A61K 2236/00* (2013.01); *A61K 2236/331* (2013.01); *A61K 2236/333* (2013.01)

(58) Field of Classification Search
None
See application file for complete search history.

(56) References Cited

FOREIGN PATENT DOCUMENTS

| | | |
|---|---|---|
| EP | 1 466 608 A1 | 10/2004 |
| EP | 1 466 608 B1 | 5/2006 |
| JP | 4055951 B2 | 12/2007 |
| JP | 2009-001513 A | 1/2009 |
| JP | 2010-222293 A | 10/2010 |
| JP | 2012-193157 A | 10/2012 |
| JP | 2014-136679 A | 7/2014 |
| KR | 10-2002-0089817 | 11/2002 |

(Continued)

OTHER PUBLICATIONS

Jo et al. (KR 10-0506396 B1 Korea Atomic Energy Research), Aug. 10, 2005, pp. 1-18, also contained within the IDS (Year: 2005).*
Jung et al. "Protective Effects of New Herbal Composition (MH-30) against Radiation Injuries in Hematopoietic and Self-Renewal Tissues" *J. Korean Soc. Food Sci. Nutr.* 45(7):948-957 (2016).

(Continued)

*Primary Examiner* — Michael Barker
*Assistant Examiner* — Randall Winston
(74) *Attorney, Agent, or Firm* — Klarquist Sparkman, LLP

(57) ABSTRACT

The present invention relates to a method for preparing an herbal composition with increased fat-soluble polyphenols, an herbal composition prepared by the method, and a use of the composition. The herbal composition with increased fat-soluble polyphenols of the present invention is characterized by the significantly increased content of fat-soluble polyphenols including decursin, compared with the herbal composition of comparative example, and also demonstrates a significant anti-oxidative activity, immune cell activating effect, and cancer cell growth inhibitory effect, significantly reduces renal toxicity and liver toxicity induced by the anticancer agent cisplatin back so as to be almost normal condition, and significantly inhibits the intestinal crypt loss caused by irradiation, compared with the herbal composition of comparative example. Therefore, the herbal composition with increased fat-soluble polyphenols of the present invention can be effectively used as a composition for cancer treatment, an anti-cancer adjuvant, a composition for enhancing immune function, a composition for protecting a living body, and a composition for preventing side effects of cancer treatment.

4 Claims, 12 Drawing Sheets

(56) References Cited

FOREIGN PATENT DOCUMENTS

| KR | 10-2005-0053046 | 6/2005 |
|----|-----------------|--------|
| KR | 10-0506384 | 7/2005 |
| KR | 10-0506396 | 8/2005 |
| KR | 10-2006-0104408 | 10/2006 |
| KR | 10-2012-0120515 | 11/2012 |
| KR | 10-2013-0022856 | 3/2013 |
| KR | 10-2014-0123444 | 10/2014 |

OTHER PUBLICATIONS

Won et al. "Simultaneous Quantification of Three Marker Compounds in Samultang by HPLC/DAD" *Kor. J. Pharmacogn.* 40(4):298-302 (2009).

Jeong et al. "Quantitative Analysis of Marker Compounds in *Angelica gigas, Angelica sinensis*, and *Angelica acutiloba* by HPLC/DAD" 63(7):504-511 (2015).

Kim et al. "Immunomodulatory and Antidiabetic Effects of a New Herbal Preparation (HemoHIM) on Streptozotocin-Induced Diabetic Mice" *Evidence-Based Complementary and Alternative Medicine* vol. 2014, Article ID 461685 (8 pages) http://dx.doi.org/10.1155/2014/461685.

\* cited by examiner

METHOD FOR PREPARING HERBAL COMPOSITION HAVING INCREASED FAT-SOLUBLEPOLYPHENOL CONTENT, HERBAL COMPOSITION PREPARED THEREBY AND USE THEREOF

CROSS REFERENCE TO RELATED APPLICATIONS

This is the U.S. National Stage of International Application No. PCT/KR2016/011314, filed Oct. 10, 2016, which in turn claims the benefit of Korean Patent Application No. 10-2015-0141824, filed Oct. 8, 2015, all of which are incorporated herein in their entirety.

TECHNICAL FIELD

The present invention relates to a method for preparing an herbal composition with increased fat-soluble polyphenols, an herbal composition prepared by the method, and a use of the composition.

BACKGROUND ART

The method for the treatment of cancer can be divided into a method of direct killing cancer cells such as surgery, administration of an anticancer agent, and irradiation; and a method of activating immune function in vivo to remove cancer cells such as immunotherapy. Conventionally, the method of direct killing has been mainly used, but recently, it has been used in combination with immunotherapy in the treatment of cancer.

Since the immune response mechanism was disclosed recently, many attempts have been made to treat cancer by using immunomodulators. Immunomodulators stimulate immune cells in vivo nonspecifically to enhance the immune function, thereby increasing the body's defense against disease factors. Such nonspecific immunomodulators are exemplified by killed bacterial bodies, chemically synthesized substances (synthesized nucleic acid derivatives or glycosides), and biological agents (cytokines or hormones), etc. Studies are being made to obtain anticancer effect by increasing in vivo immune function by administering the said materials above. However, most of those nonspecific immunomodulators are limited in clinical use because of toxicity or side effects. In particular, since various cytokines involved in immune response were identified, studies to mass produce those cytokines by genetic engineering method and apply them to cancer therapy have been actively undergoing. However, the studies are limited because of a severe toxicity caused thereby. In the course of cancer treatment via using an anti-cancer agent or radio-therapy, severe side effects such as hematopoietic disorder and self-renewal tissue damage can be accompanied. Such side effects are attributed to oxidative tissue damage caused by the anticancer agent or radiation.

As a study on substances that can protect a living body from radiation, there was a report made in 1949 saying that cystein containing thiol group displays the radioprotective effects. Since then, aminothiol derivatives (especially WR series) have been studied intensively. However, because of the toxicity of aminothiol derivatives, the practical application has been limited. Thereafter, the protective effects of chemical synthetics such as dipyridamole, adenosine monophosphate, and deoxyspergualin have been studied, but they have also been limited in practical application due to toxicity. Another attempt has been made to obtain the protective effect by stimulating hematopoietic and immune system using polysaccharides such as glucan and detoxified bacterial bodies such as OK-432, which have been studied as anticancer immunomodulators. However, they are also limited in practical use due to side effects. It is tried recently to obtain the radiation protection effect by using cytokines involved in immune response and hematopoietic function including interleukin-1, tumor necrosis factor (TNF), granulocyte colony-stimulating factor (GM-CSF), hormones. However, these agents are also applied limitedly due to toxicity.

Therefore, it is urgently requested to develop a safe material that can increase anticancer effect, immune function, and hematopoietic function and at the same time can protect a living body from side effects caused by irradiation. Recent studies are focused on natural bioactive substances without side effects. In particular, since oxidative damage caused by harmful reactive oxygen species or free radicals as well as radiation or chemical substances has been revealed as a cause of various diseases such as aging-related diseases and cancer, studies are undergoing with antioxidants to prevent and treat these diseases. Bioactive substances efficient in body regulation and protection have been screened actively from natural substances and some of them are now commercialized as health supplementary foods or therapeutic agents.

Korean Patent No. 10-0506384 describes about the herbal composition and its preparation method of herb mixture for cancer inhibition, recovery of immune system and protection of body from oxidative damage, wherein an herbal composition prepared from a herb mixture comprising *Angelica Radix, Cnidium Rhizoma*, and *Paeonia Radix* was confirmed to demonstrate the anticancer effect, immune function improvement effect, hematopoietic function improvement effect, and radiation protection effect. However, the herbal composition was prepared only by the hot water extraction method. So, the content of fat-soluble polyphenols in the composition was low, suggesting that the composition did not have sufficiently high medicinal effect for the inhibition of cancer cell growth and the prevention of side effects caused by anticancer agents and radiation.

The present inventors tried to develop an herbal composition with a more significant medicinal effect than the herbal composition of comparative example (Korean Patent No. 10-0506384) by increasing the content of fat-soluble polyphenols. In the course of our study, unlike the herbal composition of comparative example developed based on the hot water extract, the inventors believed that the composition based on the aqueous ethanol extract prepared by appropriate ethanol concentration could have significantly increased fat-soluble polyphenols while maintaining the water-soluble polyphenol content at the similar level. Based on the thought, the present inventors prepared an herbal composition capable of exhibiting various activities together and proving their excellent activity, leading to the completion of the present invention. Briefly, the inventors mixed *Angelica Radix, Cnidium Rhizoma*, and *Paeonia Radix*, resulting in the preparation of an herb mixture. A certain portion of herb mixture aqueous ethanol extract was taken and stored. The remaining portion of the herb mixture aqueous ethanol extract, and the hot water extract were mixed, followed by ethanol precipitation. The precipitated polysaccharides were mixed with the stored portion of aqueous ethanol extract to prepare the herbal composition. (It will be described in detail in examples). The herbal composition comprising the polysaccharides above and the aqueous ethanol extract contains the significantly higher content of fat-soluble polyphenols including decursin, and shows more significant anti-oxidative activity and immune cell activation effect, inhibits cancer cell growth, significantly reduces renal toxicity and liver toxicity caused by the anticancer agent cisplatin almost back to the normal level, and has a significant inhibitory effect on intestinal crypt loss caused by irradiation, by confirming which the present inventors completed this invention.

DISCLOSURE

Technical Problem

It is an object of the present invention to provide a method for preparing an herbal composition with increased fat-soluble polyphenols, an herbal composition prepared by the method, and a use of the same.

Technical Solution

To achieve the above object, the present invention provides a method for preparing an herbal composition with increased fat-soluble polyphenols comprising the following steps:

1) preparing an aqueous ethanol extract from the herb mixture composed of *Angelica Radix, Cnidium Rhizoma,* and *Paeonia Radix;*

2) preparing a hot water extract from the herb mixture composed of *Angelica Radix, Cnidium Rhizoma,* and *Paeonia Radix* of step 1) above;

3) taking a certain portion of the aqueous ethanol extract of step 1) for the later use for the preparation of the mixture of step 4), and mixing the other remaining portion of aqueous ethanol extract above and the hot water extract of step 2), followed by ethanol precipitation to obtain polysaccharides; and 4) mixing the portion of the aqueous ethanol extract of step 1) taken aside and the polysaccharides of step 3).

The present invention also provides an herbal composition with increased fat-soluble polyphenols prepared by the method of the present invention.

The present invention also provides a pharmaceutical composition for the prevention and treatment of cancer which comprises the herbal composition of the invention as an active ingredient.

The present invention also provides a health functional food for the prevention of cancer and improvement of body defense which comprises the herbal composition of the invention as an active ingredient.

The present invention also provides an anticancer adjuvant comprising the herbal composition of the invention as an active ingredient.

The present invention also provides a pharmaceutical composition for preventing side effects of anticancer treatment which comprises the herbal composition of the invention as an active ingredient.

The present invention also provides a health functional food for preventing side effects of anticancer treatment which comprises the herbal composition of the invention as an active ingredient.

The present invention also provides a pharmaceutical composition for enhancing immune function which comprises the herbal composition of the invention as an active ingredient.

The present invention also provides a health functional food for enhancing immune function which comprises the herbal composition of the invention as an active ingredient.

The present invention also provides a pharmaceutical composition for the protection of a living body from oxidative damage which comprises the herbal composition of the invention as an active ingredient.

The present invention also provides a health functional food for the protection of a living body from oxidative damage which comprises the herbal composition of the invention as an active ingredient.

The present invention also provides a method for the prevention or treatment of cancer containing the step of administering the herbal composition above to a subject.

The present invention also provides a method for the inhibition of side effects accompanied by anticancer treatment containing the step of administering the herbal composition above to a subject.

The present invention also provides a method for increasing the effect of cancer treatment containing the step of administering the herbal composition of the invention to a subject.

The present invention also provides a use of the herbal composition of the invention as a composition for the prevention or treatment of cancer.

The present invention also provides a use of the herbal composition of the invention as a health functional food for the prevention of cancer and improvement of body defense.

The present invention also provides a use of the herbal composition of the invention as an anticancer adjuvant.

The present invention also provides a use of the herbal composition of the invention as a pharmaceutical composition for the prevention of side effects accompanied by anticancer treatment.

In addition, the present invention provides a use of the herbal composition of the invention as a health functional food for the prevention of side effects accompanied by anticancer treatment.

Advantageous Effect

The herbal composition with increased fat-soluble polyphenols of the present invention is characterized by a significantly increased content of fat-soluble polyphenols including decursin, compared with the herbal composition of comparative example; displays a more significant antoxidative activity, immune cell activation effect, and cancer cell growth inhibition effect; reduces significantly renal toxicity and liver toxicity caused by the anticancer agent cisplatin; and displays a more significant inhibition effect of intestinal crypt loss caused by irradiation. Therefore, the herbal composition with increased fat-soluble polyphenols of the present invention can be effectively used as a composition for treating cancer, an anticancer adjuvant, a composition for preventing side effects accompanied by anticancer treatment, a composition for enhancing immune function, and a composition for protecting a living body.

DESCRIPTION OF DRAWINGS

The application of the preferred embodiments of the present invention is best understood with reference to the accompanying drawings, wherein.

BEST MODE

Figure 1:
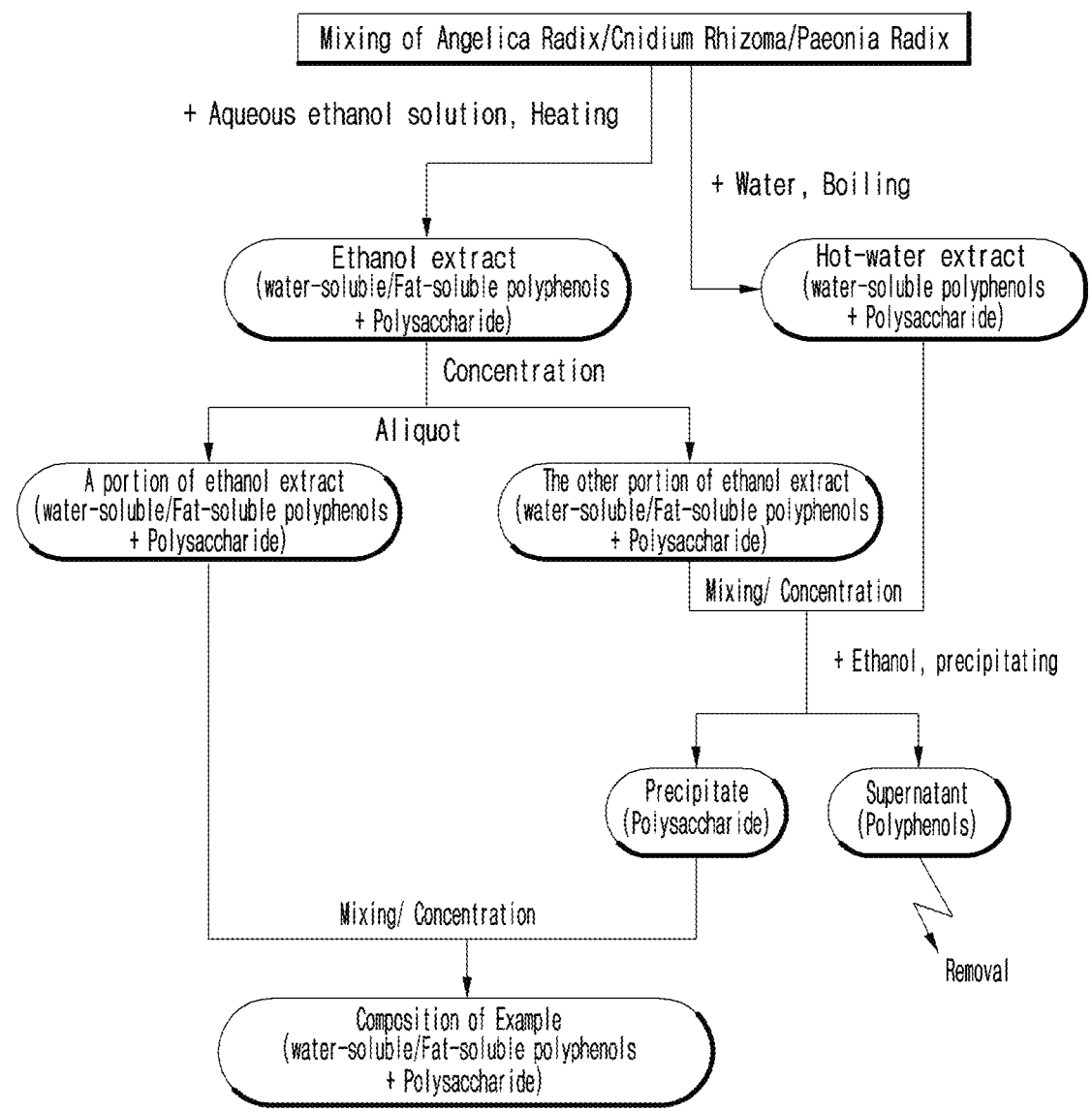
FIG. 1 is a diagram illustrating the preparation process of the herbal composition with increased fat-soluble polyphenols according to an example.

Hereinafter, the present invention is described in detail.

The present invention provides a method for preparing an herbal composition with increased fat-soluble polyphenols comprising the following steps:

1) preparing an aqueous ethanol extract from the herb mixture composed of *Angelica Radix, Cnidium Rhizoma*, and *Paeonia Radix;*

2) preparing a hot water extract from the herb mixture composed of *Angelica Radix, Cnidium Rhizoma*, and *Paeonia Radix* of step 1) above;

3) taking a certain portion of the aqueous ethanol extract of step 1) for the later use for the preparation of the mixture of step 4), and mixing the other remaining portion of aqueous ethanol extract above and the hot water extract of step 2), followed by ethanol precipitation to obtain polysaccharides; and 4) mixing the portion of the aqueous ethanol extract of step 1) taken aside and the polysaccharides of step 3).

The present invention also provides an herbal composition with increased fat-soluble polyphenols prepared by the method of the present invention.

In step 1) and step 2), *Angelica Radix, Cnidium Rhizoma*, and *Paeonia Radix* can be either purchased or cultivated, and more preferably *Angelica gigas Radix, Cnidium officinale Rhizoma*, and *Paeonia lactiflora Radix*, but not always limited thereto. Any parts of *Angelica Radix, Cnidium Rhizoma*, and *Paeonia Radix*, such as leaves, stems, roots, and flowers can be used.

The herbal mixture of step 1) and step 2) is characteristically prepared by mixing *Angelica Radix, Cnidium Rhizoma*, and *Paeonia Radix*. At this time, the mixing ratio is 1:0.5-1.5:0.5-1.5, preferably 1:0.8-1.2:0.8-1.2, and more preferably 1:1:1.

The aqueous ethanol extract of step 1 is prepared preferably with 10-50% ethanol, and more preferably with 20-35% ethanol. The volume of ethanol added to the herb mixture composed of *Angelica Radix, Cnidium Rhizoma*, and *Paeonia Radix* is 5-20 times the weight of the mixture, preferably 10-15 times, and more preferably 10 times the weight of the mixture. The ethanol extraction is performed by heating the mixture. At this time, the extraction time is preferably 1-5 hours, more preferably 1-3 hours, and most preferably 2 hours. If the extraction time is less than 1 hour, full extraction is not expected. If the extraction time is more than 5 hours, despite the extraction can be fully performed, the extract can be denaturized due to the continued heating. By extracting with 20-35% aqueous ethanol solution as a solvent, the extract includes not only water-soluble polyphenols but also higher contents of fat-soluble polyphenols and some of polysaccharides as well.

To prepare the hot-water extract of step 2), water was added to the herb mixture composed of *Angelica Radix, Cnidium Rhizoma*, and *Paeonia Radix* at the volume of 2-20 times the weight of the mixture, preferably 5-15 times, and more preferably 5-10 times the weight of the mixture. The extraction is performed by boiling the mixture. At this time, the extraction time is preferably 1-7 hours, more preferably 1-5 hours, and most preferably 2-4 hours. If the extraction time is less than 1 hour, full extraction is not expected. If the extraction time is longer than 7 hours, despite the extraction can be performed fully, the extract can be denaturized due to the continued heating. The hot-water extract above characteristically includes not only water-soluble polyphenols but also a large amount of polysaccharides.

The polysaccharides of step 3) can be obtained by the following procedure: the other remaining portion of the aqueous ethanol extract is mixed with the hot-water extract, and then 100% ethanol is added thereto to attain 80% aqueous ethanol solution, and lastly the mixture stands for some time to precipitate polysaccharides. For the precipitation, ethanol is added preferably at the volume of 1-7 times the volume of the mixture comprising the aqueous ethanol extract and the hot-water extract, more preferably 2-5 times, and most preferably 4 times the volume of the mixture is added according to the preferred embodiment of the present invention. If the volume of ethanol is less than 1 time the volume of the mixture, that amount is not enough to precipitate polysaccharides. If the volume of ethanol is more than 7 times the volume of the mixture, it would be a waste because that amount would be more than enough. The precipitation is preferably induced at room temperature for 18-48 hours, more preferably for 24-36 hours, and most preferably for 24 hours.

In the mixing procedure in step 4, the polysaccharides are included as to attain the proportion of 10-50 weight % in the resulting mixture, more preferably at the proportion of 20-40 weight %, and most preferably at the proportion of 30-35 weight % according to the preferred embodiment of the present invention. If the content of the polysaccharides in the final herbal composition with increased fat-soluble polyphenols of the invention is less than 10 weight %, the activity induced by the polysaccharides would not be fully induced. On the other hand, if the content is more than 50 weight %, the weight % of the fat-soluble or water-soluble polyphenols that can make the herbal composition to have various activities would be lowered, indicating the activity induced by the composition would not be fully induced. Therefore, it is preferred for the herbal composition with increased fat-soluble polyphenols to contain the polysaccharides at the proportion of 30-35 weight % and then the activities induced not only by the polysaccharides but also by the fat-soluble polyphenols and the water-soluble polyphenols would be significant.

The fat-soluble polyphenols are preferably selected from the group consisting of nodakenin and decursin, but not always limited thereto.

In a preferred embodiment of the present invention, the present inventors mixed *Angelica Radix, Cnidium Rhizoma*, and *Paeonia Radix* at the ratio of 1:1:1 to make an herb mixture. The mixture was added with 30% aqueous ethanol solution, and then heated to prepare an aqueous ethanol extract. The extract was recovered and water was added to the residue and boiled to prepare a hot-water extract. A certain portion of the aqueous ethanol extract was aliquoted and stored for the later use in the preparation of the final mixture. The other remaining portion of aqueous ethanol extract and the hot-water extract were mixed together, followed by concentration. 100% ethanol was added to the mixed extracts to attain 80% aqueous ethanol solution, which stood at room temperature. As a result, the precipitated polysaccharides were obtained. Then, the portion of the aqueous ethanol extract stored above was mixed with the polysaccharides, resulting in the preparation of the herbal composition with increased fat-soluble polyphenols. The ingredients of the composition were analyzed. As a result, the fat-soluble polyphenols such as nodakenin and decursin were significantly increased in the composition, compared with the other composition of the comparative example (see FIG. 3 and Table 1).

The present invention also provides a pharmaceutical composition for the prevention and treatment of cancer which comprises the herbal composition of the invention as an active ingredient.

The present invention also provides a method for the prevention or treatment of cancer containing the step of administering the herbal composition above to a subject.

The present invention also provides a use of the herbal composition of the invention as a composition for the prevention or treatment of cancer.

The herbal composition above is preferably extracted from the herb mixture composed of *Angelica Radix, Cnidium Rhizoma*, and *Paeonia Radix* at the ratio of 1:1:1, and is characterized by containing increased fat-soluble polyphenols. To increase the proportion of fat-soluble polyphenols in the herbal composition, a portion of 30% aqueous ethanol extract is mixed with the polysaccharides obtained from the mixture of the other remaining portion of 30% aqueous ethanol extract and the hot-water extract by ethanol precipitation. At this time, the preferable proportion of the polysaccharides in the final herbal composition is 30-35 weight %.

As a result, the herbal composition of the present invention is prepared by mixing the aqueous ethanol extract containing both water-soluble polyphenols and fat-soluble polyphenols at a large amount with the polysaccharides, so that the composition contains all of the water-soluble polyphenols, the fat-soluble polyphenols, and the polysaccharides at an appropriate ratio. Therefore, the composition displays various activities induced by the components above at the significant level. In the meantime, the composition of the comparative example is prepared based on the hot-water extract, so that it mainly contains the water-soluble polyphenols and the polysaccharides, which is different from the composition of the present invention.

The cancer herein is preferably selected from the group consisting of colorectal cancer, stomach cancer, prostate cancer, breast cancer, melanoma, kidney cancer, liver cancer, brain tumor, lung cancer, uterine cancer, colon cancer, bladder cancer, and pancreatic cancer, but not always limited thereto.

In a preferred embodiment of the present invention, the present inventors treated the herbal composition with increased fat-soluble polyphenols prepared by the method of the invention to B16 mouse melanoma cells, A549 human lung cancer cells, and MDA-MB-231 human breast cancer cells, and then investigated the effect thereof. As a result, compared with the herbal composition of comparative example, the composition with increased fat-soluble polyphenols of the invention displayed more significant cancer cell growth inhibition effect (see FIGS. 6 and 7). Therefore, it was confirmed that the herbal composition with increased fat-soluble polyphenols of the present invention can be effectively used as a composition for the treatment of cancer.

The herbal composition with increased fat-soluble polyphenols of the present invention can include, in addition to the components mentioned above, one or more effective ingredients having the same or similar function to the components.

The composition of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive herein is preferably added by 0.1-90 weight part to the composition, but not always limited thereto.

That is, the composition of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the composition of the present invention with one or more suitable excipients such as starch, calcium carbonate, sucrose, lactose, and gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, and glycerogelatin, etc.

The composition of the present invention can be administered orally or parenterally in accordance with the desired method, and the parenteral administration includes external skin application, intraperitoneal injection, intrarectal injection, subcutaneous injection, intravenous injection, intramuscular injection and intrathoracic injection. The effective dosage of the composition can be determined according to weight, age, gender, health condition, diet, administration period, administration method, excretion and severity of a disease.

The composition of the present invention is administered in a pharmaceutically effective dose. The term "pharmaceutically effective dose" herein indicates the amount enough to treat the disease with applicable, reasonable or risky concentration. The dose can be determined by considering many factors such as the type of inflammatory disease, severity of the disease, activity of the drug, sensitivity to the drug, administration frequency and pathway, excretion, term of treatment, co-treatment drug and other factors regarded as relevant in the medicinal field. The composition of the present invention can be administered as an individual therapeutic agent or in combination with other therapeutic agents, sequentially or concurrently with the conventional therapeutic agents, and can be administered singly or multiply. It is important to take into account all of the above factors and to administer the amount in which the maximum effect can be obtained in a minimal amount without side effects, which can be easily determined by those in the art.

Particularly, the effective dose of the composition of the present invention can be determined according to age, gender, and weight of patient. In general the effective dose is preferably 1 mg-200 mg/kg and more preferably 10 mg-200 mg/kg, which can be administered every day or every other day, or 1-3 times a day. However, the effective dose can be increased or decreased according to the administration pathway, severity of disease, gender, body weight, and age of patient, etc, so that the effective dose above cannot limit the present invention in any aspects.

The present invention also provides a health functional food for the prevention and prevention of cancer and improvement of body defense which comprises the herbal composition of the invention as an active ingredient.

The present invention also provides a use of the herbal composition of the invention as a health functional food for the prevention of cancer and improvement of body defense.

The herbal composition above is preferably extracted from the herb mixture composed of *Angelica Radix*, *Cnidium Rhizoma*, and *Paeonia Radix* at the ratio of 1:1:1, and is characterized by containing increased fat-soluble polyphenols. To increase the concentration of fat-soluble polyphenols in the herbal composition, a portion of 30% aqueous ethanol extract is mixed with the polysaccharides obtained from the mixture of the other remaining portion of 30% aqueous ethanol extract and the hot-water extract by ethanol precipitation. At this time, the preferable proportion of the polysaccharides in the final herbal composition is 30-35 weight %.

The herbal composition of the present invention is prepared by mixing the aqueous ethanol extract containing both water-soluble polyphenols and fat-soluble polyphenols at a large amount with the polysaccharides, so that the composition contains all of the water-soluble polyphenols, the fat-soluble polyphenols, and the polysaccharides at an appropriate ratio. Therefore, the composition displays various activities induced by the components above at the significant level.

The cancer herein is preferably selected from the group consisting of colorectal cancer, stomach cancer, prostate cancer, breast cancer, melanoma, kidney cancer, liver cancer, brain tumor, lung cancer, uterine cancer, colon cancer, bladder cancer, and pancreatic cancer, but not always limited thereto.

In a preferred embodiment of the present invention, the present inventors treated the herbal composition with increased fat-soluble polyphenols prepared by the method of the invention to B16 mouse melanoma cells, A549 human lung cancer cells, and MDA-MB-231 human breast cancer cells, and then investigated the effect thereof. As a result, compared with the herbal composition of comparative example, the composition with increased fat-soluble polyphenols of the invention displayed more significant cancer cell growth inhibition effect (see FIGS. 6 and 7). Therefore, it was confirmed that the herbal composition with increased fat-soluble polyphenols of the present invention can be effectively used as a health functional food for the prevention of cancer and improvement of body defense.

The herbal composition with increased fat-soluble polyphenols of the present invention can be used as food additive. In that case, the herbal composition with increased fat-soluble polyphenols can be added as it is or as mixed with other food components according to the conventional method.

The food herein is not limited. For example, the herbal composition with increased fat-soluble polyphenols of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xylitol, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 g and more preferably 0.02-0.03 g in 100 g of the composition.

In addition to the ingredients mentioned above, the health food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The health food of the present invention can also include fruit flesh addable to natural fruit juice, fruit beverages and vegetable beverages. All the mentioned ingredients can be added singly or together. The mixing ratio of those ingredients does not matter in fact, but in general, each can be added by 001-0.1 weight part per 100 weight part of the composition of the present invention.

The present invention also provides an anticancer adjuvant comprising the herbal composition of the invention as an active ingredient.

The present invention also provides a method for increasing the effect of cancer treatment containing the step of administering the herbal composition of the invention to a subject.

The present invention also provides a use of the herbal composition of the invention as an anticancer adjuvant.

Figure 9A:
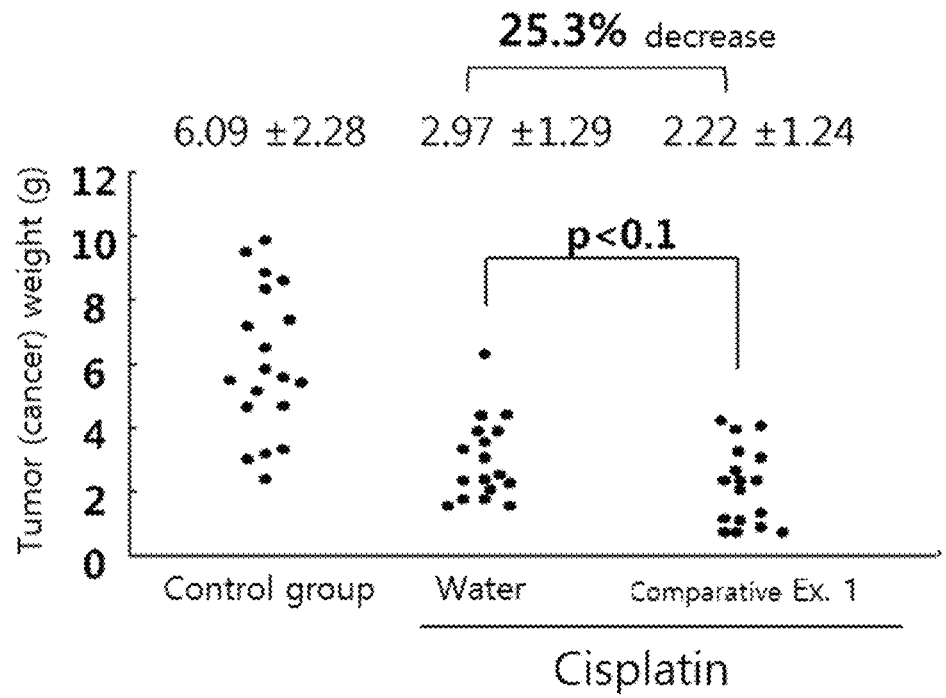
FIGS. 9A and 9B is a set of graphs illustrating the inhibitory effect of the herbal composition with increased fat-soluble polyphenols and the herbal composition of comparative example on the cancer cell growth confirmed in a mouse model:
Control group: non-treated group;
Water: water treated group;
Comparative Example 1: the group treated with the herbal composition of comparative example; and
Example 1: the group treated with the herbal composition with increased fat-soluble polyphenols.
Figure 9B:
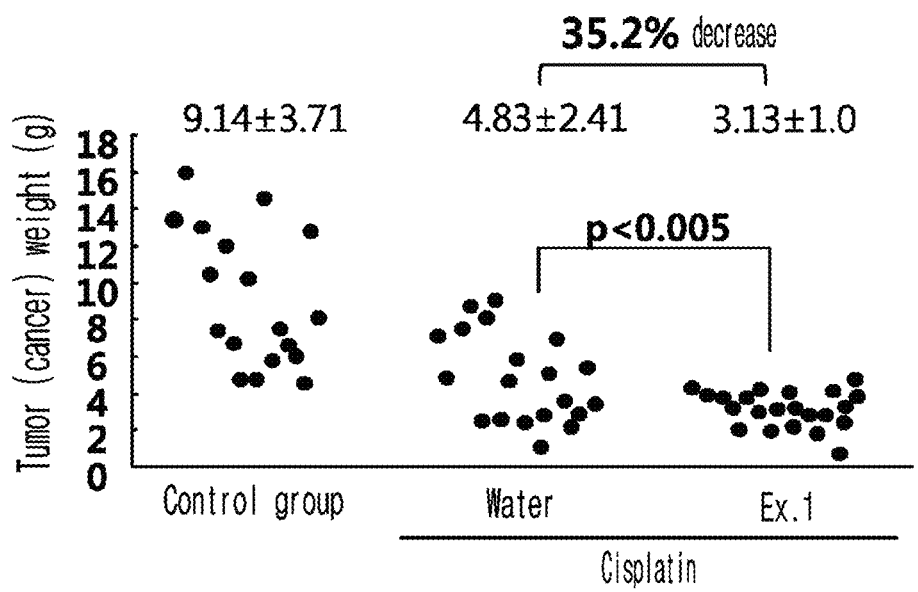

In a preferred embodiment of the present invention, the present inventors confirmed that when the herbal composition with increased fat-soluble polyphenols prepared by the method of the invention was treated to a mouse model transplanted with melanoma cells together with the anticancer agent cisplatin, the cancer tissue growth was inhibited more efficiently than when the composition of the comparative example was treated (see FIG. 9). The present inventors also confirmed that when the herbal composition with increased fat-soluble polyphenols was treated to a mouse model, the renal toxicity and liver toxicity caused by anticancer agents could be reduced (see FIGS. 10 and 11). Therefore, it was confirmed that the herbal composition with increased fat-soluble polyphenols could be effectively used as an anticancer adjuvant.

The herbal composition of the present invention can be administered independently before or after the administration of an anticancer agent, or can be co-treated with an anticancer agent simultaneously as an adjuvant. When the herbal composition of the present invention is co-treated with an anticancer agent as an anticancer adjuvant, the ratio to the anticancer agent can be adjusted according to the condition of patient, the dose of the platinum-based anticancer agent, and the administration period of the anticancer agent, etc. For example, the composition can be administered at the ratio of 0.01-10 times the total weight of the anticancer agent.

The present invention also provides a pharmaceutical composition for preventing side effects of anticancer treatment which comprises the herbal composition of the invention as an active ingredient.

The present invention also provides a health functional food for preventing side effects of anticancer treatment which comprises the herbal composition of the invention as an active ingredient.

The present invention also provides a method for the inhibition of side effects accompanied by anticancer treatment containing the step of administering the herbal composition above to a subject.

The present invention also provides a use of the herbal composition of the invention as a pharmaceutical composition for the prevention of side effects accompanied by anticancer treatment.

In addition, the present invention provides a use of the herbal composition of the invention as a health functional food for the prevention of side effects accompanied by anticancer treatment.

The side effects accompanied by anticancer treatment can include the anticancer agent mediated side effects and the radiotherapy mediated side effects. The anticancer agent mediated side effects indicate the toxicity induced by an anticancer agent, wherein the anticancer agent includes all the anticancer agents known to cause renal toxicity and liver toxicity. The anticancer agent causing toxicity herein is preferably a platinum-based anticancer agent. The platinum-based anticancer agent can be selected from the group consisting of cisplatin, carboplatin, oxaliplatin, nedaplatin, and a mixture thereof. The side effects herein include all the diseases induced by the toxicity in cells or tissues induced by the administration of an anticancer agent. In a preferred embodiment of the present invention, the toxicity is preferably renal toxicity or liver toxicity. The side effects accompanied by radiotherapy can include cell or tissue damage. In a preferred embodiment of the present invention, the side effect is preferably intestinal crypt loss.

Figure 10:
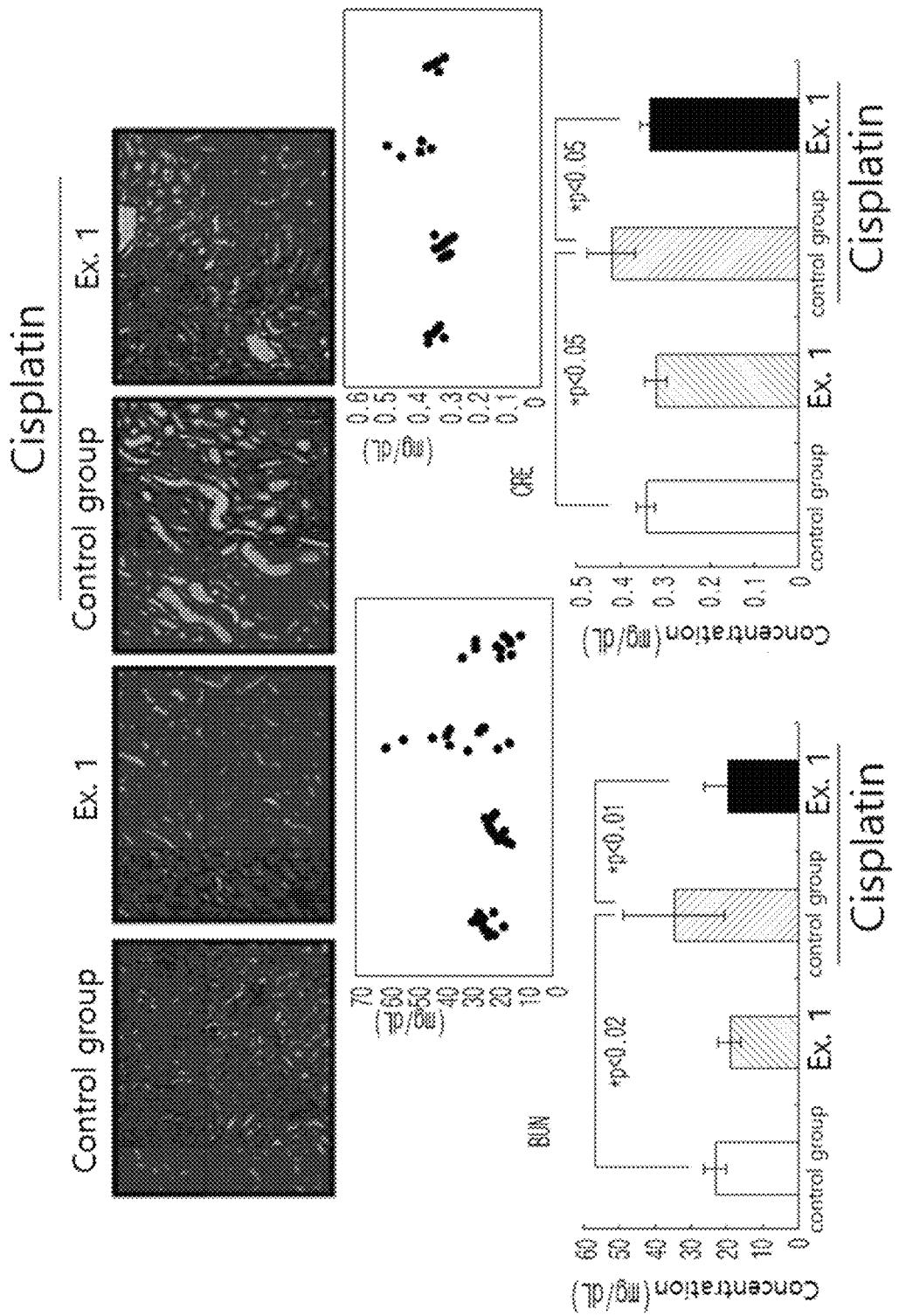
FIG. 10 is a set of photographs and graphs illustrating the renal toxicity reducing effect of the herbal composition with increased fat-soluble polyphenols:
Control group: water treated group;
Example 1: the group treated with the herbal composition with increased fat-soluble polyphenols;
BUN: blood urea nitrogen; and
CRE: creatinine.
Figure 11:
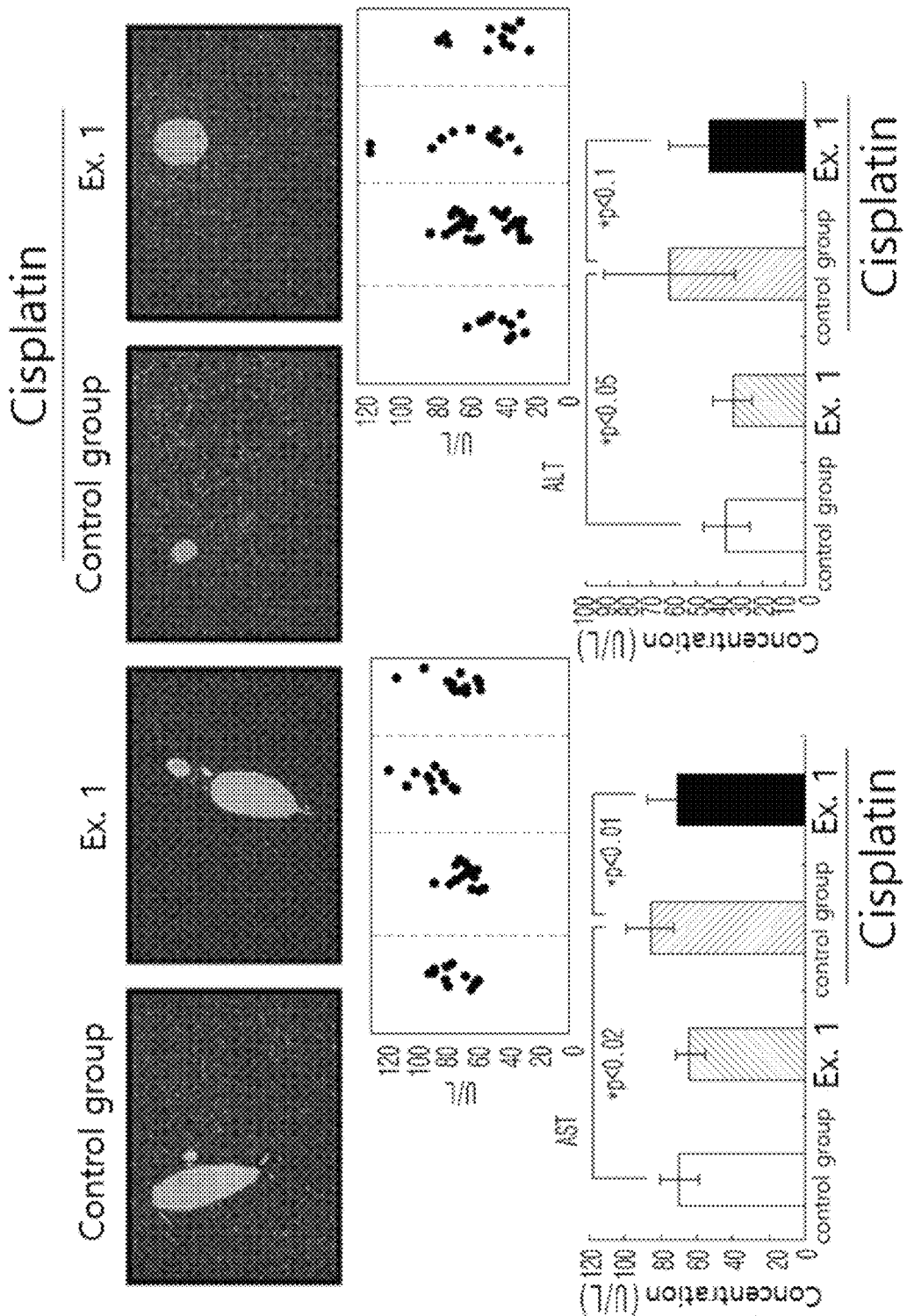
FIG. 11 is a set of photographs and graphs illustrating the liver toxicity reducing effect of the herbal composition with increased fat-soluble polyphenols:
Control group: water treated group;
Example 1: the group treated with the herbal composition with increased fat-soluble polyphenols;
AST: aspartate aminotransferase; and
ALT: alanine aminotransferase.

In a preferred embodiment of the present invention, when the herbal composition with increased fat-soluble polyphenols prepared by the method of the present invention was administered to a mouse model, the renal toxicity and liver toxicity caused by the administration of an anticancer agent were reduced (see FIGS. 10 and 11). Therefore, it was confirmed that the herbal composition with increased fat-soluble polyphenols of the present invention could be used as a composition for the prevention of side effects accompanied by anticancer treatment.

Figure 12A:
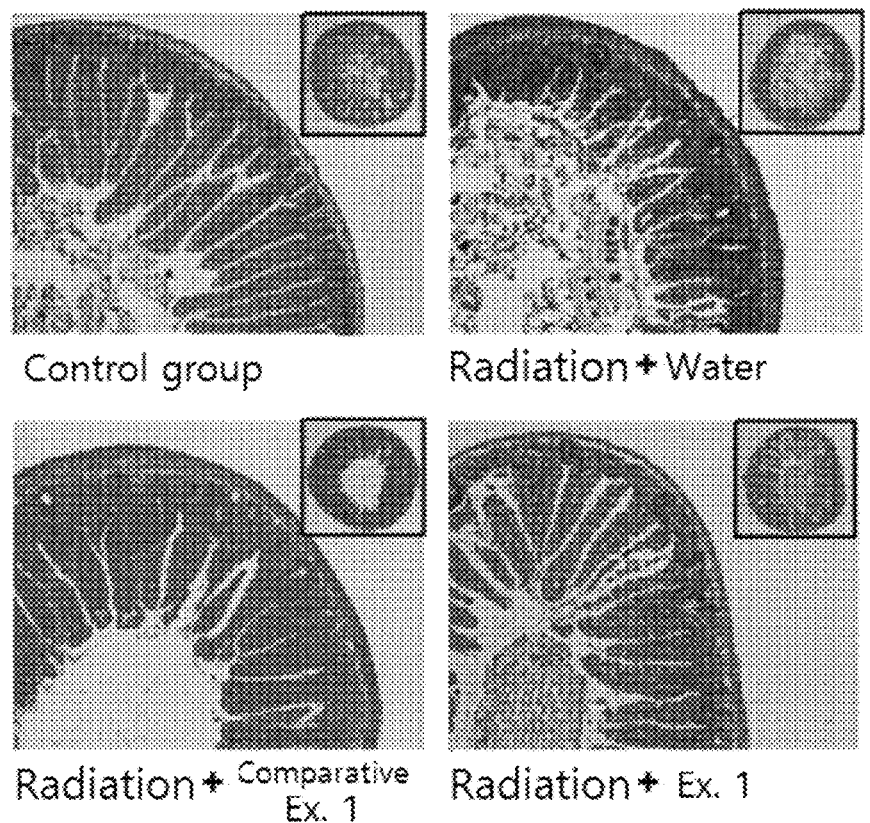
FIGS. 12A and 12B is a set of photographs and a graph illustrating the self-renewal tissue (intestinal crypt) protection effect of the herbal composition with increased fat-soluble polyphenols and the herbal composition of comparative example against radiation in a mouse model:
Control group: non-treated group;
Radiation+Water: The group treated with water combined with irradiation;
Radiation+Comparative Example 1: the group treated with the herbal composition of comparative example combined with the irradiation;
Radiation+Example 1: the group treated with the herbal composition with increased fat-soluble polyphenols combined with the irradiation;
Water: water treated group;
Comparative Example 1: the group treated with the herbal composition of comparative example; and
Example 1: the group treated with the herbal composition with increased fat-soluble polyphenols.
Figure 12B:
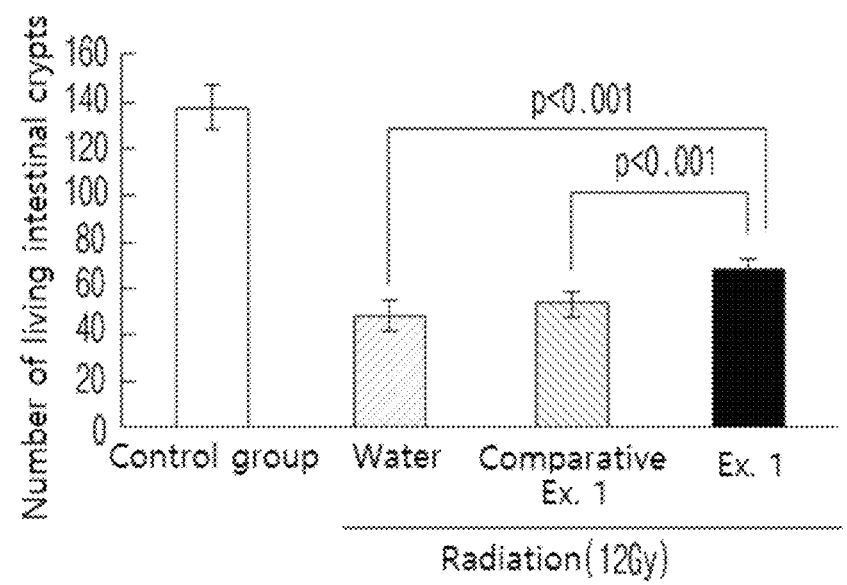

It was also confirmed that the herbal composition with increased fat-soluble polyphenols could inhibit intestinal crypt loss more significantly than the herbal composition of comparative example did (see FIG. 12 and Table 2). Therefore, it was confirmed that the herbal composition with increased fat-soluble polyphenols above could be used as a composition for the prevention of side effects caused by radiotherapy.

The present invention also provides a pharmaceutical composition for enhancing immune function which comprises the herbal composition of the invention as an active ingredient.

The present invention also provides a health functional food for enhancing immune function which comprises the herbal composition of the invention as an active ingredient.

Figure 5:
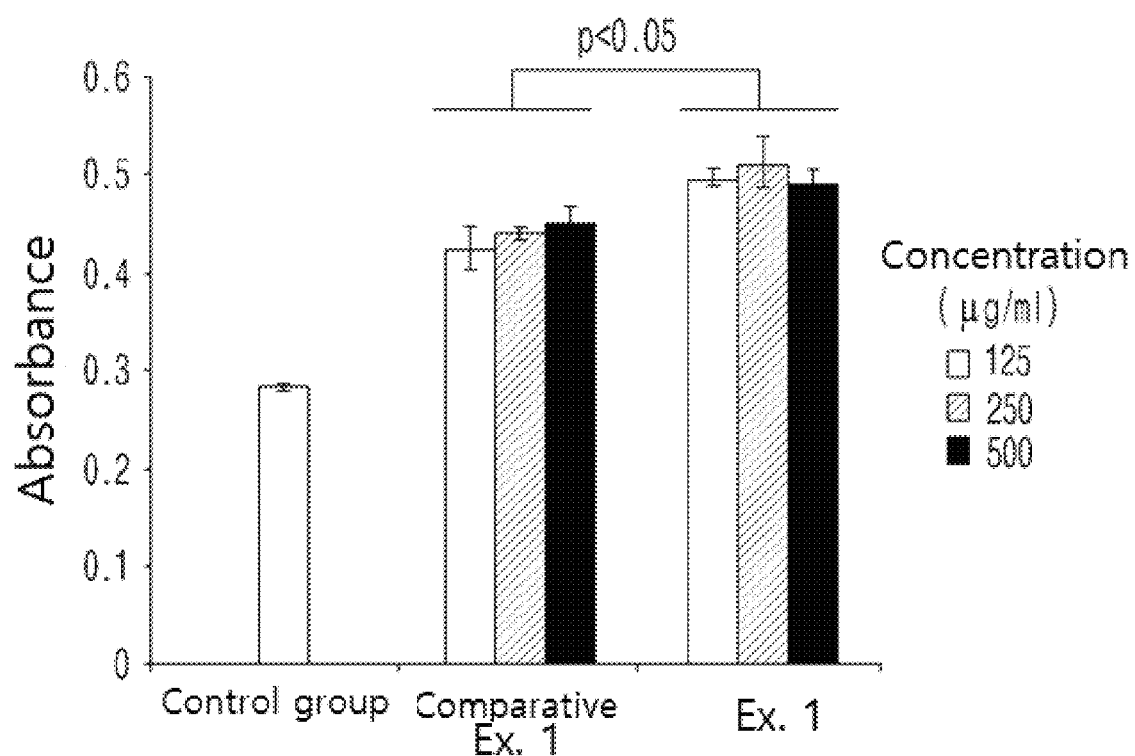
FIG. 5 is a graph illustrating the immune cell activation effect of the herbal composition with increased fat-soluble polyphenols and the herbal composition of comparative example:
Comparative Example 1: herbal composition of comparative example; and
Example 1: herbal composition with increased fat-soluble polyphenols.

In a preferred embodiment of the present invention, the present inventors confirmed that the herbal composition with increased fat-soluble polyphenols prepared by the method of the invention could activate lymphocytes, the immune cell cells, more significantly than the herbal composition of comparative example (see FIG. 5). Therefore, it was confirmed that the herbal composition with increased fat-soluble polyphenols above could be used as a composition for enhancing immune function.

The present invention also provides a pharmaceutical composition for the protection of a living body from oxidative damage which comprises the herbal composition of the invention as an active ingredient.

The present invention also provides a health functional food for the protection of a living body from oxidative damage which comprises the herbal composition of the invention as an active ingredient.

In a preferred embodiment of the present invention, the present inventors compared the herbal composition with increased fat-soluble polyphenols prepared by the method of the invention with the herbal composition of comparative example. As a result, it was confirmed that the herbal composition with increased fat-soluble polyphenols of the invention had more significant hydroxyl radical and superoxide anion scavenging activity that could cause oxidative damage directly than the composition of the comparative example (see FIG. 4), indicating that the herbal composition with increased fat-soluble polyphenols of the invention could be useful as a composition for the protection of a living body from oxidative damage.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of the Herbal Composition with Increased Fat-Soluble Polyphenols Prepared by Using 30% Aqueous Ethanol Extract Three herbs, *Angelica Radix* (*Angelica gigas* Nakai), *Cnidium Rhizoma* (*Cnidium officinale* Makino), and *Paeonia Radix* (*Paeonia lactiflora* Pallas), listed in Korean Food Standards Codex as food raw materials, were dried in the shade and cut into pieces and then mixed together at the same weight ratio. 30% aqueous ethanol solution was added to the herb mixture at the volume of 10 times the weight of the herb mixture, followed by boiling at 70° C. for 2 hours to recover the aqueous ethanol extract. Then, distilled water was added to the remaining residue at the volume of 10 times the weight of the herb mixture, boiled for 2-6 hours, and extracted to recover the hot-water extract. A portion of the aqueous ethanol extract was aliquoted and stored, and the remaining aqueous ethanol extract and the hot-water extract were mixed. The mixture was concentrated, to which 100% ethanol was added at the volume of 4 times the volume of the mixture. The mixture stood at room temperature for 24 hours, and the precipitate was recovered to prepare a polysaccharide fraction. The stored portion of the 30% aqueous ethanol extract and the polysaccharide fraction were mixed to prepare an herbal composition in which the fat-soluble polyphenol components were increased and 30-35 weight % of polysaccharide was included (referred as the herbal composition with increased fat-soluble polyphenols, hereinafter). In this preparation process of the present invention, it is preferred to determine the amount of the aqueous ethanol extract portion in order to make the proportion of the polysaccharides in the final mixture could be 30-35 weight %.

The preparation procedure of the herbal composition with increased fat-soluble polyphenols is shown in FIG. 1 (FIG. 1).

Comparative Example 1: Preparation of Herbal Composition by Hot-Water Extraction Three herbs, *Angelica Radix* (*Angelica gigas* Nakai), *Cnidium Rhizoma* (*Cnidium officinale* Makino), and *Paeonia Radix* (*Paeonia lactiflora* Pallas), listed in Korean Food Standards Codex as food raw materials, were dried in the shade and cut into pieces and then mixed together at the same weight ratio. Distilled water was added to the herb mixture at the volume of 10 times the weight of the herb mixture, boiled for 8-10 hours, and extracted to prepare the hot-water extract. ¼-⅔ of the hot-water extract was stored and ethanol was added to the remaining ⅓-¾ of the hot-water extract, resulting in 80% aqueous ethanol solution. The mixture stood at room temperature (5-15° C.) overnight and then a precipitate was recovered to prepare a polysaccharide fraction. The polysaccharide fraction was added to the stored hot-water extract, wherein the proportion of the polysaccharides was preferably adjusted at 30-40 weight %. As a result, an herbal composition was prepared via hot-water extraction (referred as the herbal composition of comparative example, hereinafter).

Figure 2:
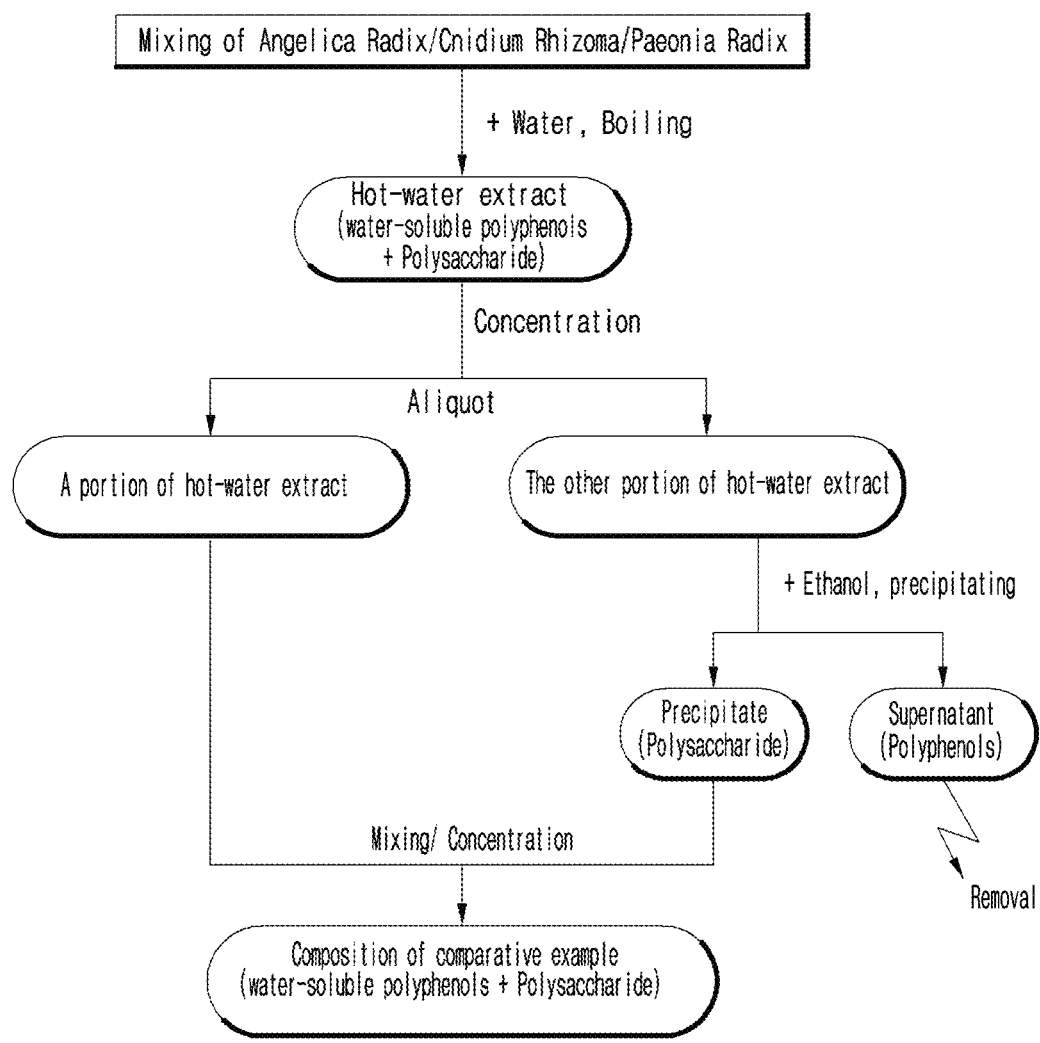
FIG. 2 is a diagram illustrating the preparation process of the herbal composition of comparative example.

The preparation procedure of the herbal composition of comparative example is shown in FIG. 2 (FIG. 2).

Example 2: Comparison of Components Between the Herbal Composition with Increased Fat-Soluble Polyphenols and the Herbal Composition of Comparative Example To compare the components of the herbal composition each prepared by the method of example 1 and the method of comparative example 1 according to the extraction and preparation method, HPLC fingerprinting analysis was performed.

Particularly, 100% ethanol was added to each sample at the volume of 4 times by the weight of the sample, and each mixture stood at 4° C. for 12 hours. Centrifugation was performed at 4000×g for 10 minutes to obtain the supernatant polyphenol fraction layer. The polyphenol fraction obtained from each sample was concentrated under reduced pressure, resulting in the 50 mg/ml of sample each. HPLC fingerprinting analysis was performed with those samples. First, the concentrated sample was filtered (0.45 μm, PTFE filter) and loaded in HPLC at the volume of 10 μl. LC-20A HPLC (Shimadzu, Japan) was used for the analysis and the separation of ingredients was performed by the gradient of a moving phase (0.1% formic acid aqueous solution and 100% MeCN (acetonitrile; $CH_3CN$)) using C18-PAQ (Cosmosil, Japan). The peak of each component was detected using a 230 nm detector. As a result, a fingerprinting graph was obtained. To quantify each index component, gallic acid, chlorogenic acid, albiflorin, paeoniflorin, benzoic acid, nodakenin, and decursin were dissolved in 50% aqueous methanol solution at the concentration of 4.5-900 mg/ml respectively, based on which a standard calibration curve was made. The peak area of each component on the fingerprinting graph was calculated to quantify the content thereof.

Figure 3:
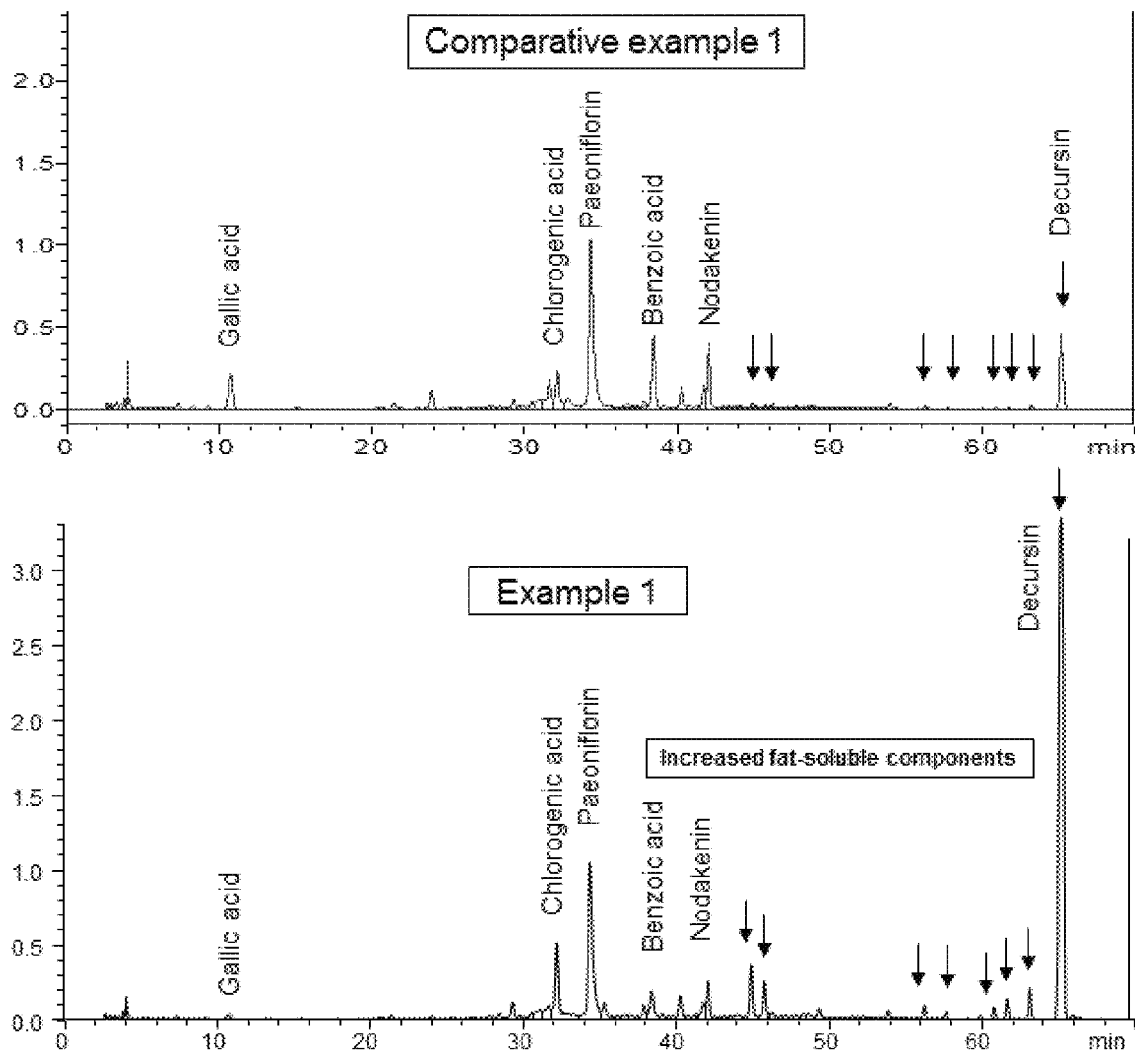
FIG. 3 is a set of graphs illustrating the difference in components between the herbal composition with increased fat-soluble polyphenols and the herbal composition of comparative example:
Comparative Example 1: herbal composition of comparative example; and
Example 1: herbal composition with increased fat-soluble polyphenols.

As a result, as shown in FIG. 3 and Table 1, the content of fat-soluble polyphenols in the herbal composition with increased fat-soluble polyphenols of the present invention was significantly increased, compared with the herbal composition of comparative example. In particular, the content of decursin was significantly increased, suggesting that there was a difference in the content of the components in the herbal composition prepared from the herb mixture composed of *Angelica Radix, Cnidium Rhizoma*, and *Paeonia Radix* according to the extraction solvent and the extraction method. Particularly, the content of decursin was increased about 9 times and the content of nodakenin was increased 1.2 times. In addition, at least seven or more various components indicated by arrows in FIG. 3 were significantly increased (Table 1 and FIG. 3).

That is, when the aqueous ethanol extract was used for the preparation of the herbal composition of example 1, the content of fat-soluble polyphenols was significantly increased therein, compared with when the hot-water extract was used.

Experimental Example 1: Antioxidant Activity of the Herbal Composition with Increased Fat-Soluble Polyphenols To compare the antioxidant activity between the herbal composition with increased fat-soluble polyphenols prepared by the method of example 1 and the herbal composition of comparative example 1, the scavenging activities against hydroxyl radical and superoxide anion, which are reactive molecules causing direct damage in biological macromolecules such as DNA, protein and lipid, was first investigated by the following experiment.

Particularly, to measure the hydroxyl radical scavenging activity, 0.10 ml of 0.2 mM $FeCl_3$, 0.1 ml of 0.1 mM EDTA, 0.1 ml, of 10 mM 2-deoxyribose, and 0.1 ml, of 0.1 mM ascorbic acid were mixed in a test tube. 0.05 ml of the herbal composition with increased fat-soluble polyphenols, the herbal composition of comparative example, or the polyphenol fraction of each herbal composition was mixed with 0.45 ml, of 0.1M phosphate buffer (pH7.4) and 0.2 ml, of 10 mM $H_2O_2$, followed by reaction in a 37° C. water bath for 1 hour. 0.5 ml, of 5% TCA (trichloroacetic acid) solution was added thereto to terminate the reaction, and then 0.5 ml of 1% TBA (2-thiobarbituric acid) solution was added thereto. The reaction mixture was boiled in a water bath at 100° C. for 10 minutes, and then cooled down. Then, $OD_{532}$ was measured by using UV-spectrophotometer (Shimadzu UV-1201, Japan). The hydroxyl radical scavenging activity was calculated by using the difference of absorbance between the sample group and the control group according to the mathematical formula 1 below. The result is presented as %.

Hydroxyl radical scavenging activity (%)={1−(AS−AO)/(AC−AO)}×100       Mathematical Formula 1

AO: absorbance of the negative control group not treated with the sample and $H_2O_2$;

AC: absorbance of the control group not treated with the sample but treated with $H_2O_2$; and AS: absorbance of the experimental group treated with the sample and $H_2O_2$.

Figure 4A:
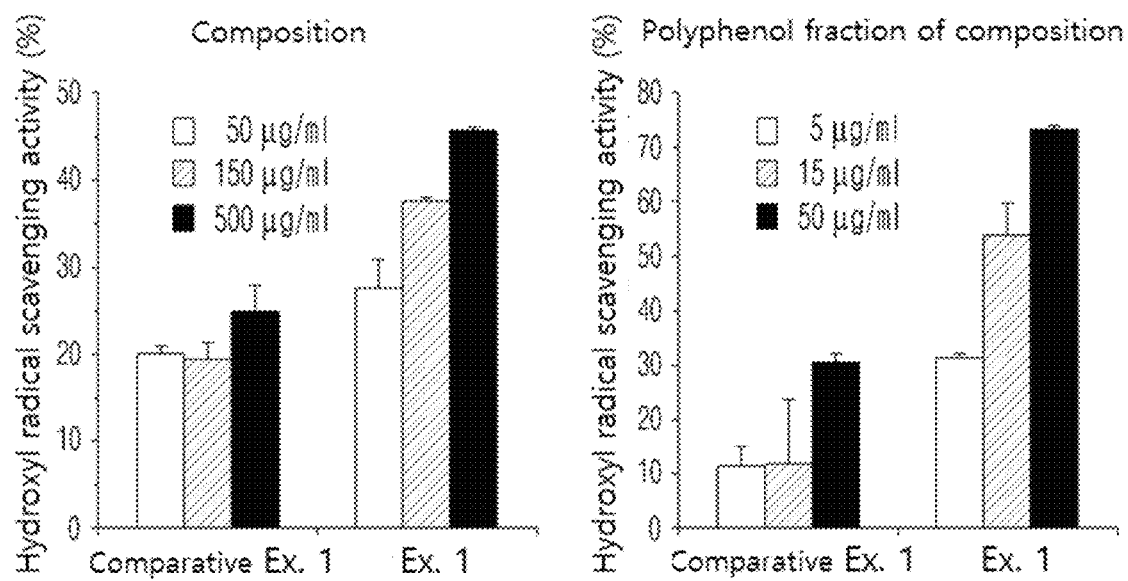
FIGS. 4A and 4B is a set of graphs illustrating the anti-oxidative activity of the herbal composition with increased fat-soluble polyphenols, the herbal composition of comparative example, and the polyphenol fractions of each composition:
Comparative Example 1: herbal composition of comparative example; and
Example 1: herbal composition with increased fat-soluble polyphenols.

As a result, as shown in FIG. 4A, the herbal composition with increased fat-soluble polyphenols displayed about 1.4 times-1.9 times higher hydroxyl radical scavenging activity than the herbal composition of comparative example showed (FIG. 4A). In the meantime, the activity of the polyphenol fractions of each composition was also investigated. As a result, the polyphenol fraction obtained from the herbal composition with increased fat-soluble polyphenols of the present invention demonstrated at least 2.5 times higher hydroxyl radical scavenging activity than the polyphenol fraction of the herbal composition of comparative example. Therefore, it was proved that the increase of fat-soluble polyphenols was the major reason of increasing the radical

TABLE 1

| | Content of Major Component (μg/ml) | | | | | | |
|---|---|---|---|---|---|---|---|
| | Gallic acid | Chlorogenic acid | Albiflorin | Paeoniflorin | Benzoic acid | Nodakenin | Decursin |
| Example 1 | 78.2 | 143.2 | 180.8 | 593.2 | 80.8 | 234.8 | 360.5 |
| Comparative Example 1 | 78.0 | 77.8 | 185.4 | 590.6 | 72.0 | 192.2 | 41.3 | scavenging activity. Hydroxyl radicals are massively generated when water molecules are cleaved by radiation. So, the herbal composition with increased fat-soluble polyphenols of the present invention was confirmed to have the radiation damage protection activity by scavenging the hydroxyl radicals significantly.

To measure the superoxide anion scavenging activity, 5 μl of the herbal composition with increased fat-soluble polyphenols, the herbal composition of comparative example, or the polyphenol fractions of each herbal composition was added as a sample to 50 μl of 100 mM sodium phosphate (pH7.4) containing 10 mU/ml of xanthine oxidase along with 5 μl of CCK-8 (Dojindo Molecular Technologies, Rockville, ML, USA), followed by stabilization at room temperature for 1 minute. Then, 40 μl of 2.5 mM xanthine solution was added thereto, followed by reaction. Immediately after the start of the reaction and 20 minutes after the initiation of the reaction, $OD_{450}$ was measured to calculate the absorbance change. The superoxide anion scavenging activity was calculated by using the difference of absorbance between the sample group and the control group according to the mathematical formula 2 below. The result is presented as %.

Superoxide anion scavenging activity (%)={1−(*AS*−*AO*)/(*AC*−*AO*)×100    Mathematical Formula 2

AO: absorbance of the negative control group not treated with the sample and xanthine;

AC: absorbance of the control group not treated with the sample but treated with xanthine; and AS: absorbance of the experimental group treated with the sample and xanthine.

Figure 4B:
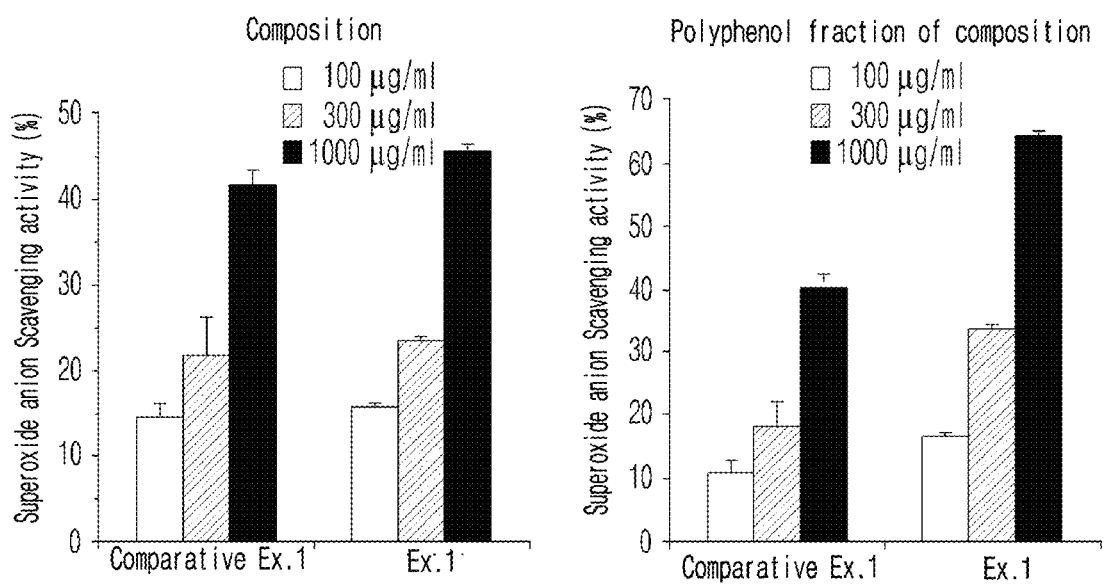

As a result, as shown in FIG. 4B, the herbal composition with increased fat-soluble polyphenols displayed at least similar or higher superoxide anion scavenging activity than the herbal composition of comparative example, suggesting that the herbal composition with increased fat-soluble polyphenols had enough antioxidant activity (FIG. 4B). In the meantime, the activity of the polyphenol fractions of each composition was also investigated. As a result, the herbal composition with increased fat-soluble polyphenols demonstrated about 1.6 times higher superoxide anion scavenging activity than the herbal composition of comparative example, indicating that the increase of fat-soluble polyphenols was the major reason of increasing the superoxide anion scavenging activity.

Experimental Example 2: Effect of the Herbal Composition with Increased Fat-Soluble Polyphenols on Immune Cell Activation To investigate the effect of the herbal composition with increased fat-soluble polyphenols prepared by the method of example 1 and the herbal composition of comparative example on the immune cell activation, each sample was treated to the immune cells (lymphocytes) separated from spleen, followed by the observation of the immune cell activation. Once the immune cells are activated, cell metabolism increases and cells proliferate. So, the proliferation of immune cells was measured by investigating absorbance using CCK-8 reagent (Dojindo Molecular Technologies, Rockville, ML, USA).

Particularly, the spleen was aseptically extracted from a mouse and the splenocytes were separated. After removing red blood cells using Tris-NH$_4$Cl solution, the cells were washed twice with HBSS to prepare splenic lymphocytes. The splenic lymphocytes were seeded in a 96-well culture plate at the density of $2 \times 10^5$ cells/0.2 ml per each well. The herbal composition with increased fat-soluble polyphenols or the herbal composition of comparative example was added thereto at different concentrations, followed by culture for 3 days. Upon completion of the culture, CCK-8 reagent was treated to each well (10 μl/well), followed by further culture for 4 hours. Then, $OD_{450}$ was measured (ref. 650 nm), followed by evaluation of the proliferative capacity of the splenic lymphocytes induced by each sample.

As a result, as shown in FIG. 5, the herbal composition with increased fat-soluble polyphenols demonstrated significantly higher immune cell activating effect than the herbal composition of comparative example (FIG. 5).

Experimental Example 3: Inhibitory Effect of the Herbal Composition with Increased Fat-Soluble Polyphenols on Cancer Cell Growth In Vitro <3-1> Confirmation of Inhibitory Effect of the Herbal Composition with Increased Fat-Soluble Polyphenols on Cancer Cell Growth in Cell Culture Models To investigate the cancer cell growth inhibitory effect of the herbal composition with increased fat-soluble polyphenols prepared by the method of example 1 and the herbal composition of comparative example in various cancers, the cancer cell growth inhibitory effect was measured in B16 mouse melanoma cells, A549 human lung cancer cells, and MDA-MB-231 human breast cancer cells as follows.

Particularly, B16 mouse melanoma cells were seeded in a 96-well plate at the density of $5 \times 10^4$ cells/well, to which the herbal composition with increased fat-soluble polyphenols and the herbal composition of comparative example were treated at the different concentrations of 50, 100, 200, and 500 μg/ml in the total culture volume of 200 μl. The cells were cultured in a cell culture incubator. Forty-eight hours after the incubation, 10 μl of CCK-8 solution was added to each well, followed by further culture for 4 hours. Then, $OD_{450}$ was measured to investigate the cell growth.

A549 human lung cancer cells and MDA-MB-231 human breast cancer cells were seeded in a 96-well plate, to which the herbal composition with increased fat-soluble polyphenols and the herbal composition of comparative example were treated at the different concentrations of 125, 250, and 500 μg/ml in the total culture volume of 200 μl, followed by culture in a cell culture incubator. Considering the different proliferation rate of each cell line, the cell survival rate was measured after two cycles of cell division after the sample treatment. To do so, 20 μl of MTT (Sigma-Aldrich Co., St. Louis, Mo., USA) solution (5 mg/ml) was added to A549 cells 48 hours after the sample treatment and to MDA-MB-231 cells 72 hours after sample treatment, followed by further culture for 2 hours. After eliminating the cell culture medium, 200 μl of DMSO (dimethylsulfoxide) was added to each well, followed by stirring. Then, $OD_{565}$ was measured to investigate the cell growth.

Figure 6A:
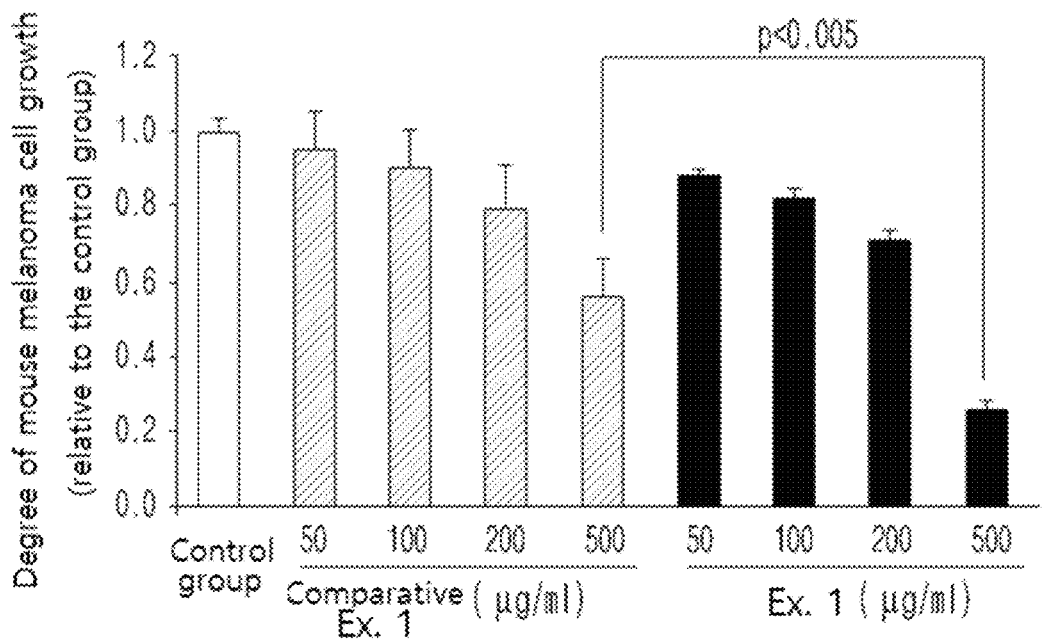
FIGS. 6A and 6B is a set of graphs illustrating the results of the in vitro investigation of the mouse cancer cell growth inhibition effect of the herbal composition with increased fat-soluble polyphenols and the herbal composition of comparative examples:
Comparative Example 1: herbal composition of comparative example; and
Example 1: herbal composition with increased fat-soluble polyphenols.
Figure 6B:
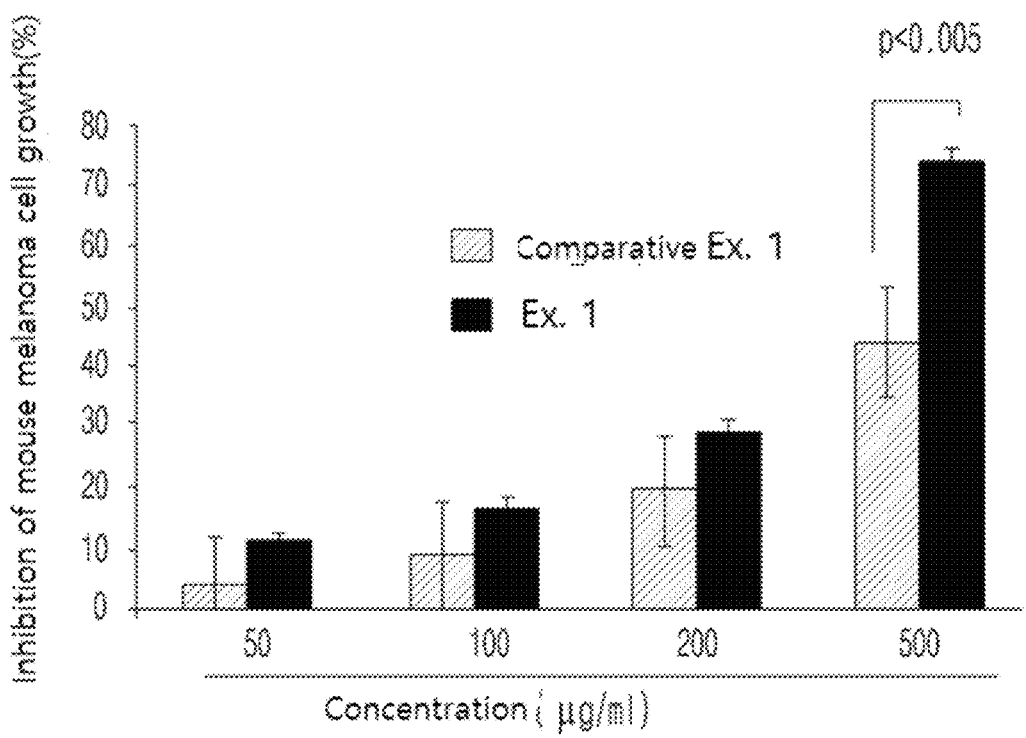

As a result, as shown in FIG. 6, the herbal composition with increased fat-soluble polyphenols demonstrated higher cancer cell growth inhibitory effect in B16 mouse melanoma cells than the herbal composition of comparative example. In particular, the herbal composition with increased fat-soluble polyphenols displayed 1.5 times higher cancer cell growth inhibitory activity at the concentration of 200 μg/ml and 1.7 times higher activity at the concentration of 500 μg/ml than the herbal composition of comparative example (FIG. 6).

Figure 7A:
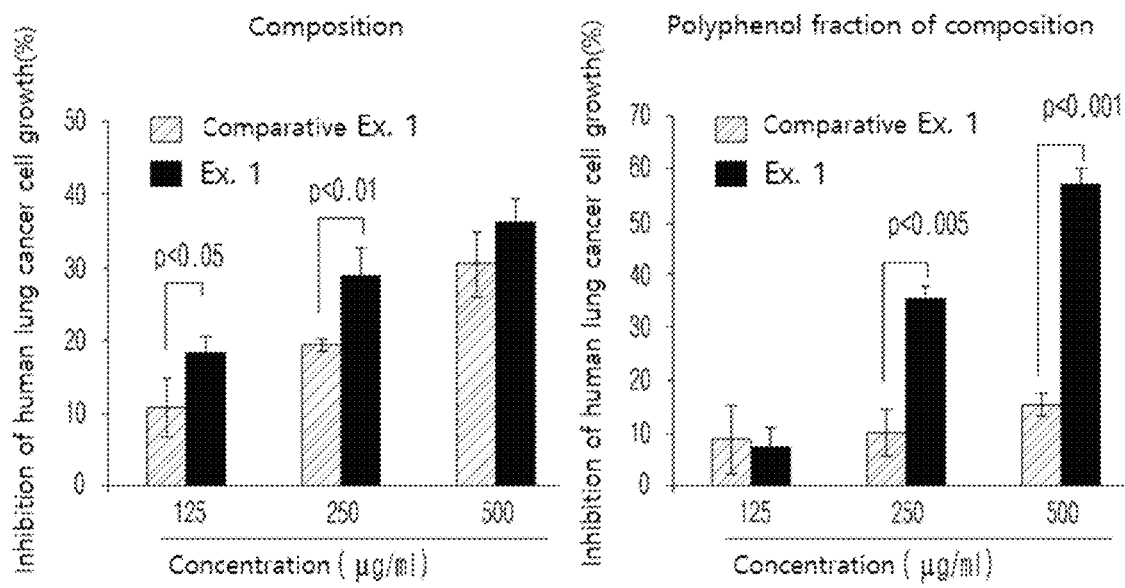
FIGS. 7A and 7B is a set of graphs illustrating the results of the in vitro investigation of the human cancer cell growth inhibition effect of the herbal composition with increased fat-soluble polyphenols, the herbal composition of comparative example, and the polyphenol fractions of each composition:
Comparative Example 1: the groups treated with the herbal composition of comparative example and the polyphenol fraction thereof; and
Example 1: the groups treated with the herbal composition with increased fat-soluble polyphenols and the polyphenol fraction thereof.
Figure 7B:
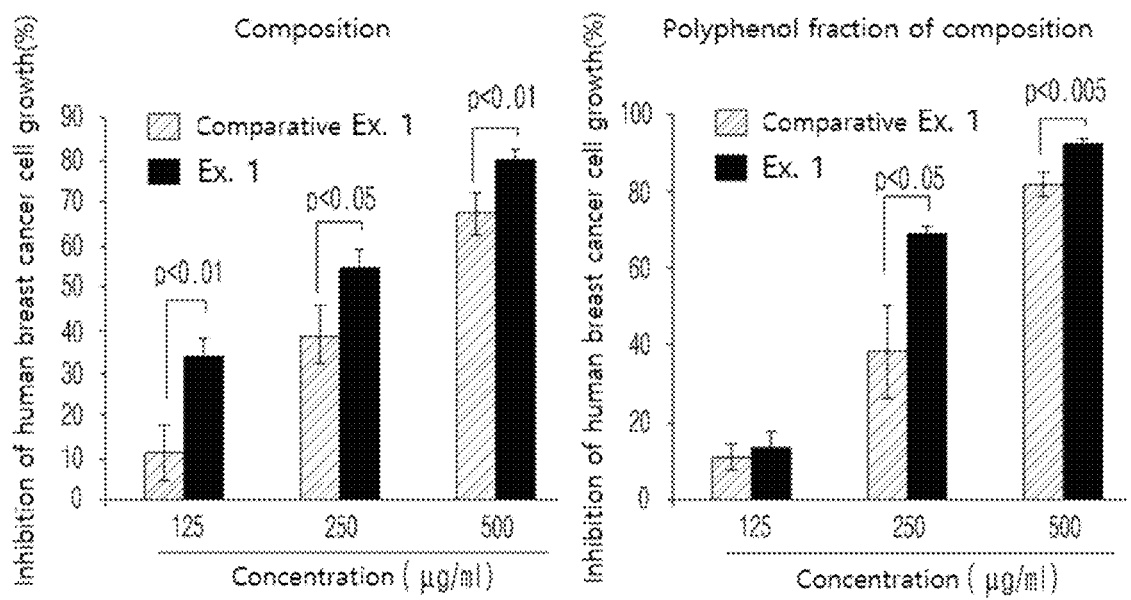

As shown in FIG. 7, the herbal composition with increased fat-soluble polyphenols showed higher cancer cell growth inhibitory activity in A549 human lung cancer cells and MDA-MB-231 breast cancer cells than the herbal composition of comparative example. Particularly, the herbal composition with increased fat-soluble polyphenols demonstrated 1.7 times higher cancer cell growth inhibitory activity at the concentration of 125 μg/ml and 1.5 times higher activity at the concentration of 250 μg/ml in A549 lung cancer cells and at the same time 3.0 times higher at the concentration of 125 μg/ml and 1.4 times higher at the concentration of 250 μg/ml in MDA-MB-231 breast cancer cells than the herbal composition of comparative example (FIG. 7). In the meantime, the activity of the polyphenol fractions of each herbal composition was measured. As a result, compared with the polyphenol fraction of the herbal composition of comparative example, the polyphenol fraction of the herbal composition with increased fat-soluble polyphenols displayed 3.5 times higher cancer cell growth inhibitory activity at the concentration of 250 μg/ml in A549 lung cancer cells and 1.7 times higher activity at the concentration of 250 μg/ml in MDA-MB-231 breast cancer cells (FIG. 7). Therefore, it was confirmed that the increase of fat-soluble polyphenols was the major reason of the increase of cancer cell growth inhibitory activity of the herbal composition with increased fat-soluble polyphenols.

The results above also confirmed that the herbal composition with increased fat-soluble polyphenols had higher cancer cell growth inhibitory activity in mouse and human cancer cells than the composition of the comparative example.

<3-2> Confirmation of Effect of the Herbal Composition with Increased Fat-Soluble Polyphenols on Normal Cell Growth in a Cell Culture Model To investigate the effect of the herbal composition with increased fat-soluble polyphenols prepared by the method of example 1 and the herbal composition of comparative example on the normal cell growth, the effect of the same on the growth of IMR-90 human lung fibroblasts was measured as follows.

Particularly, IMR-90 human lung fibroblasts were seeded in a 96-well plate, to which the herbal composition with increased fat-soluble polyphenols, the herbal composition of comparative example, and the polyphenol fractions of each composition were treated at the different concentrations of 125, 250, and 500 μg/ml in the total culture volume of 200 μl, followed by culture in a cell culture incubator. After about two cycles of the cell division, the cell survival rate was measured. To do so, 20 μl of MTT (Sigma-Aldrich Co., St. Louis, Mo., USA) solution (5 mg/ml) was added to each well 48 hours after the sample treatment, followed by further culture for 2 hours. After eliminating the cell culture medium, 200 μl of DMSO (dimethylsulfoxide) was added to each well, followed by stirring. Then, $OD_{565}$ was measured to investigate the cell growth.

Figure 8:
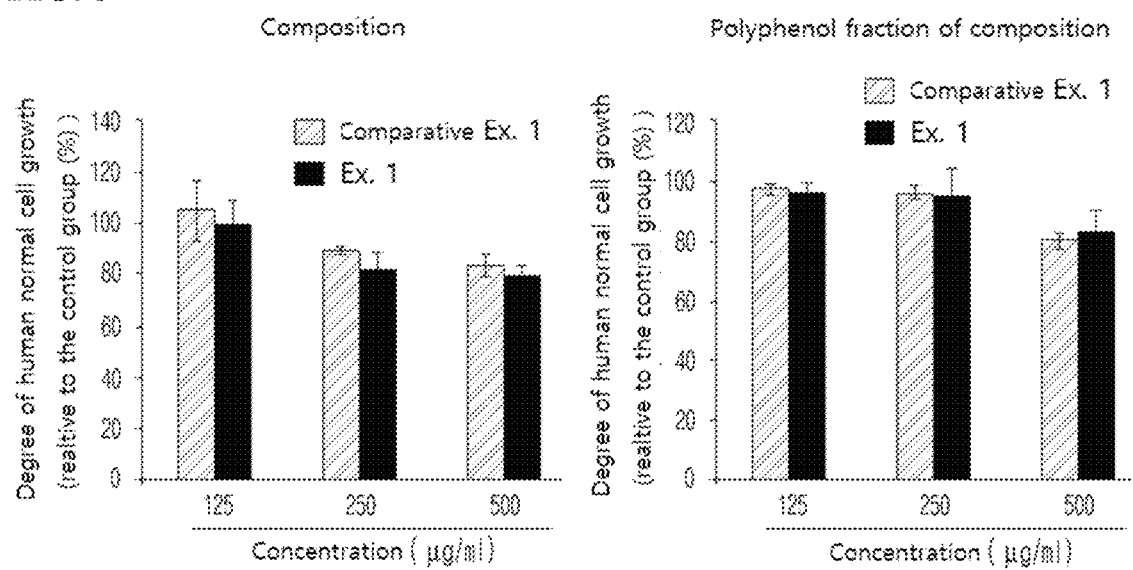
FIG. 8 is a set of graphs illustrating the results of the in vitro investigation of the effect of the herbal composition with increased fat-soluble polyphenols, the herbal composition of comparative example, and the polyphenol fractions of each composition on the human normal cell growth:
Comparative Example 1: the groups treated with the herbal composition of comparative example and the polyphenol fraction thereof; and
Example 1: the groups treated with the herbal composition with increased fat-soluble polyphenols and the polyphenol fraction thereof.

As a result, as shown in FIG. 8, the herbal composition with increased fat-soluble polyphenols, the herbal composition of comparative example, and the polyphenol fractions of each composition did not affect much on the growth of IMR-90 human lung fibroblasts, and there was no significant difference among the compositions and the fractions, either.

As described above, it was confirmed from the results of the investigation of the cancer cell growth inhibitory effect (FIGS. 6 and 7) and the effect on the normal cell growth (FIG. 8) of the compositions above that the herbal composition with increased fat-soluble polyphenols showed higher cancer cell specific inhibitory effect over the normal cells.

Experimental Example 4: Inhibitory Effect of the Herbal Composition with Increased Fat-Soluble Polyphenols on Cancer Tissue Growth in an Animal Model To investigate the cancer cell growth inhibitory effect of the herbal composition with increased fat-soluble polyphenols prepared by the method of example 1 and the herbal composition of comparative example in vivo, B16F10 melanoma cells were transplanted in a mouse. Then, the inhibitory effect of the compositions on the growth of the transplanted cancer tissue was confirmed as follows.

Particularly, $5 \times 10^5$ B16F10 melanoma cells were transplanted subcutaneously to the left femur of a 7 week old C57BL/6 mouse. From the next day of the transplantation until the animal was sacrificed, the herbal composition with increased fat-soluble polyphenols or the herbal composition of comparative example was orally administered every day at the dose of 100 mg/kg. Cisplatin, a widely used anticancer agent was intraperitoneally injected at a dose of 4 mg/kg on day 3, day 10, and day 17 from the transplantation of melanoma cells, that is the mouse was co-treated with cisplatin and the herbal composition. On day 20 from the transplantation of melanoma cells, the mouse was sacrificed and the tumor was taken out to be weighed.

As a result, as shown in FIG. 9, when the herbal composition with increased fat-soluble polyphenols was co-treated with cisplatin, the tumor growth was inhibited by 35.2%, compared with that of the group treated with cisplatin alone. When the herbal composition of comparative example was co-treated with cisplatin, the tumor growth was inhibited by 25.3%. These results indicate that the herbal composition with increased fat-soluble polyphenols has a significant inhibitory effect on the cancer tissue growth, which is about 1.39 fold higher than that of the herbal composition of comparative example (FIG. 9).

Experimental Example 5: Renal and Liver Toxicity Reducing Effect of the Herbal Composition with Increased Fat-Soluble Polyphenols in the Mouse Model Administered with an Anticancer Agent To investigate the renal and liver toxicity reducing effect of the herbal composition with increased fat-soluble polyphenols prepared by the method of example 1 in the mouse model administered with an anticancer agent, histological analysis and serum biochemical analysis were performed as follows.

Particularly, a 7 week old ICR mouse was orally administered with the herbal composition with increased fat-soluble polyphenols every day at the dose of 100 mg/kg for 20 days. Cisplatin, an anticancer agent, was intraperitoneally injected at a dose of 3 mg/kg on day 3, 4, 9, 10, 15, and 16 from the administration of the herbal composition. 24 hours after the last administration of the herbal composition, the mouse was sacrificed, followed by histological analysis and serum biochemical analysis. For the histological analysis, the kidney and the liver were extracted from the mouse, followed by fixing in 10% neutral formalin solution. The fixed tissues were embedded in paraffin according to the conventional method. Sections were prepared and stained with hematoxylin and eosin for microscopic examination. For the serological evaluation, blood was collected from the orbital vein of the mouse. Serum was separated from the collected blood and stored at −70° C. until the analysis. Then, serum biochemical analysis was performed by using AU400 automatic analyzer (Olympus, Japan). BUN (blood urea nitrogen) and CRE (creatinine) were used as the renal toxicity indices and AST (aspartate aminotransferase) and ALT (alanine aminotransferase) were used as the liver toxicity indices.

As a result, as shown in FIG. 10, it was confirmed that the damage of kidney tissue (glomeruli) and the increases of BUN (blood urea nitrogen) and CRE (creatinine), the serum biochemical indices of renal toxicity, caused by administration of cisplatin were reduced to the normal levels by administration of the herbal composition with increased fat-soluble polyphenols (FIG. 10).

As shown in FIG. 11, it was also confirmed that the increases of AST (aspartate aminotransferase) and ALT (alanine aminotransferase), the serum biochemical indices of liver toxicity, caused by administration of cisplatin were reduced to the normal levels by administration of the herbal composition with increased fat-soluble polyphenols (FIG. 11).

From the above results, it was confirmed that the herbal composition with increased fat-soluble polyphenols could be effectively used as a composition for preventing side effects of anticancer treatment since the composition could reduce the renal toxicity and liver toxicity caused by cisplatin.

Experimental Example 6: Radiation Protection Effect of the Herbal Composition with Increased Fat-Soluble Polyphenols in a Mouse Animal Model To confirm whether the herbal composition with increased fat-soluble polyphenols prepared by the method of example 1 or the herbal composition of comparative example showed the radiation protection effect in a mouse model, the intestinal crypt loss in the medium-dose-irradiated mouse was investigated by the following method.

Particularly, ICR mouse was orally administered with the herbal composition with increased fat-soluble polyphenols and the herbal composition of comparative example daily from 3 days before the irradiation until three days after the irradiation at the dose of 100 mg/kg. Whole body irradiation was performed with gamma my at the dose of 12 Gy. 3.5 days after the irradiation, the mouse was sacrificed and the small intestine was removed. 8-12 small intestine sections were prepared from each mouse, followed by embedding in paraffin according to the conventional method. The prepared paraffin sections were stained with haematoxylin and eosin. The number of intestinal crypts located at the circumference of each small intestine section of 8 specimens per mouse was counted under optical microscope and the mean and deviation of each experimental group were calculated.

As a result, as shown in Table 2 and FIG. 12, the number of intestinal crypts in the irradiated mouse model was approximately 1.3 times higher in the group treated with the herbal composition with increased fat-soluble polyphenols than in the group treated with the herbal composition of comparative example (P<0.001). The results above directly confirmed that the herbal composition with increased fat-soluble polyphenols had more significant radiation protection effect than the herbal composition of comparative example (Table 2 and FIG. 12).

TABLE 2

| Experimental Group | Number of intestinal crypt[1] | Survival Rate (%) |
|---|---|---|
| Normal Control Group | 137.6 ± 8.5 | 100 |
| Irradiated Group (12 Gy) | 47.2 ± 6.3 | 34.3 |
| Radiation (12 Gy) + Comparative Example 1 | 53.5 ± 5.2 | 38.9 |
| Radiation (12 Gy) + Example 1 | 68.4 ± 3.0** | 49.7 |

[1]8 ICR mice per experimental group (n = 8).
**showed significant increase compared with the group treated with the herbal composition of comparative example, p < 0.001.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

We claim:

1. A method for preparing an herbal composition with increased fat-soluble polyphenols comprising the following steps:
   1) extracting an herb mixture composed of *Angelica Radix, Cnidium Rhizoma*, and *Paeonia Radix* with ethanol to form an aqueous ethanol extract, and boiling the aqueous to form a residue;
   2) preparing a hot-water extract from the residue from step 1) above;
   3) mixing a first portion of the aqueous ethanol extract of step 1) and the hot-water extract of step 2) to form a mixture, and then precipitating in the mixture 66-83% ethanol to obtain polysaccharides; and
   4) mixing a second portion of the aqueous ethanol extract of step 1) and the polysaccharides of step 3), thereby preparing the herbal composition with increased fat-soluble polyphenols.

2. The method for preparing an herbal composition with increased fat-soluble polyphenols according to claim 1, wherein the herb mixture of step 1) is extracted with 10-50% ethanol.

3. The method for preparing an herbal composition with increased fat-soluble polyphenols according to claim 1, wherein the polysaccharides are mixed in step 4) at the proportion of 10-50 weight %.

4. The method for preparing an herbal composition with increased fat-soluble polyphenols according to claim 1, wherein the fat-soluble polyphenol is selected from the group consisting of nodakenin, decursin, and other polyphenols.

* * * * *